US006475162B1

United States Patent
Hu

(12) 
(10) Patent No.: US 6,475,162 B1
(45) Date of Patent: Nov. 5, 2002

(54) SYSTEM AND METHOD FOR VISION EXAMINATION USING INTERRUPT SIGNALS FOR SYNCHRONIZING VISUAL EVOKED POTENTIAL SAMPLING RATE WITH VISUAL STIMULUS

(75) Inventor: George Z. Hu, Raritan, NJ (US)

(73) Assignee: Diopsys, Inc., Metuchen, NJ (US)

( * ) Notice: Subject to any disclaimer, the term of this patent is extended or adjusted under 35 U.S.C. 154(b) by 0 days.

(21) Appl. No.: 09/924,237

(22) Filed: Aug. 7, 2001

(51) Int. Cl.$^7$ ................................................ A61B 5/00
(52) U.S. Cl. ....................................... 600/558; 600/544
(58) Field of Search ................................ 600/544, 545, 600/558; 351/205, 211, 222, 223, 237, 239

(56) References Cited

U.S. PATENT DOCUMENTS

| | | |
|---|---|---|
| 4,037,586 A | 7/1977 | Grichnik |
| 4,861,154 A | 8/1989 | Sherwin et al. |
| 4,913,160 A | 4/1990 | John |
| 4,953,968 A | 9/1990 | Sherwin et al. |
| 5,474,081 A | 12/1995 | Livingstone et al. |
| 5,638,825 A | 6/1997 | Yamazaki et al. |
| 6,044,292 A | 3/2000 | Heyrend et al. |
| 6,115,631 A | 9/2000 | Heyrend et al. |

OTHER PUBLICATIONS

An Electrophysiological Technique for Assessment of the Development of Spatial Vision, Optometry and Vision Science, vol. 74, No. 9, Sep. 9, 1997.

*Primary Examiner*—Max Hindenburg
(74) *Attorney, Agent, or Firm*—Reed Smith, LLP

(57) ABSTRACT

A system and method for performing a vision examination includes displaying a series of visual stimuli in a line by line pattern display for observation by a patient and detecting the patient's visual evoked potential in response to the visual stimuli. Electrical signals representative of the visual evoked potentials for each stimulus of each series of visual stimuli displayed is converted to digitized data, recorded and measured. The measured evoked potential data is then evaluated and compared to certain predetermined values in order to detect whether or not the measured data is reliable. The presentation of visual stimulus is synchronized with the rate of sampling the responsive visual evoked potential signals by determining if a predetermined specific line of the line by line display has been displayed and by generating interrupt request signals to a computer in order to initiate the sampling of the visual evoked potential signals and to reflash the contents of a video RAM for the next frame of image displays.

11 Claims, 6 Drawing Sheets

SYSTEM AND METHOD FOR VISION EXAMINATION USING INTERRUPT SIGNALS FOR SYNCHRONIZING VISUAL EVOKED POTENTIAL SAMPLING RATE WITH VISUAL STIMULUS

FIELD OF THE INVENTION

The present invention relates generally to the field of medical examination for diagnosis and more particularly, to a system and method for audio and visual testing by detecting and measuring evoked potentials as a result of perceived sensory stimuli. In particular, the invention is directed to a system and method for vision examination using evoked potential in which the presentation of periodic sensory stimulus and the sampling rate for recording evoked potential responsive signals are synchronized.

BACKGROUND

It is common in the field of medical examinations to assist in diagnosis to conduct various types of tests, whether conducted within a hospital environment, laboratory or physician's office. Such tests can range from simple patient observation to the use of complex examination and diagnostic equipment in which electrical stimuli are applied to a patient and the resulting electrical response signals from the patient are recorded, measured and analyzed. An electrocardiogram is an example of such an examination and diagnostic test in which electrical response signals from stimuli are recorded and analyzed. Electrocardiogram signals are indicative of a patient's heart condition and may be used to detect a heart attack or other cardiac condition. Another familiar medical diagnostic test is an electroencephalogram which uses stimuli to generate electrical signals from the brain of a patient which can be measured in the form of electrical potentials (referred to as evoked potentials) and which indicate the patient's brain activity. Data recorded from an electroencephalogram test are useful for determining such things as seizures or to assist the physician in the diagnosis of brain damage. Other examination procedures also use evoked potentials for diagnosing a variety of other diseases, including diseases of the central nervous system, auditory system and the visual system. Evoked potentials are typically determined by measuring electrical responses to sensory stimuli. When stimulation is applied to a particular sense of a human being, a corresponding brain potential is evoked at an information processing part of the brain that functions to manage the particular sense. Such evoked brain potentials are usually detected and measured by detecting electrical signals using electrodes positioned on the skin of the human head in the area of the information processing center of the brain corresponding to the particular sense involved.

Visual evoked potentials (VEP) are the evoked potentials in response to visual stimulation and are particularly useful to assist in diagnosing ophthalmic diseases in infants and young children, because such individuals are not always able to indicate responsiveness to visual stimuli or to verbalize the occurrence of vision failure. The retina contains more than 130 million light-receptor cells. These cells convert light into nerve impulses that are processed for certain features, which are transmitted by the optic nerve to the brain, where they are interpreted. Muscles attached to the eye control its movement. Birth defects, trauma from accidents, disease and age-related deterioration of the components of the eye can all contribute to eye disorders. Information processing in the brain is electrochemical in nature. Evoked potentials are the electrical responses of the brain elicited by sensory stimulation. The electrical responses of the brain produced by visual stimulation are visual evoked potentials. Changes in these visual evoked potentials can be used to pinpoint anomalies along the visual pathways. These visual pathways are interconnected linkages of cells, beginning with photoreceptor cells in the retina, passing through horizontal cells, bi-polar cells and amacrine cells to ganglion cells, which wind together to form optic nerve fibers leading to cells in the brain's thalamus which then leads to cells in the visual cortex. The retina does not register images and transmit them, unaltered, to the brain. Instead, it selects and abstracts biologically useful features of information in the patterns, which strike it, and transmits a selectively filtered message to the brain by means of interactions within and among neural networks. Further processing of the information then takes place in the brain by means of similar but more complex interactions in neural networks there. Anomalies in this electrical transmission are variations from the expected pattern in the reaction of cells along the visual pathways. They are believed to provide useful insight into many diseases and conditions affecting the brain, central nervous system, the eye and the ear. Therefore, one way to detect possible visual impairment in infants and small children is to record and measure visual evoked potentials in response to visual stimulation. Visual evoked potential analyzers can be used in screening for diseases and conditions of the brain, central nervous system, the eye and the ear. They detect abnormalities in the functioning of a patient's brain by analyzing the electrical responses of the brain, which occur when certain rapidly changing patterns of light displayed on a video screen, are viewed. These electrical responses are called potentials. Sensors attached non-invasively to the scalp permit measurements of visual evoked potentials and are widely used in basic research in vision and as an aid in the diagnoses of neurological and ophthalmic disorders. However, since these sensors record visual evoked potentials from large areas of the brain, relating changes in these recorded waves to specific neural processes has previously proven difficult or impossible.

Visual evoked potential systems have heretofore been used to test infant response to visual stimuli in order to determine the possible presence of amblyopia. Failure to detect amblyopia as early in life as possible could lead to incurable vision problems in adulthood. However, if detected early, amblyopia can be effectively treated. Accordingly, it has been found desirable to conduct visual evoked potential tests on infants and other humans. One such system, known as the VENUS System, was heretofore commercialized by Neuroscientific Corp. and is described in an article entitled "An Electrophysiological Technique for Assessment of the Development of Spatial Vision," Optometry and Vision Science, Vol. 74, No. 9, Sep. 9, 1997.

Ear infections, or otitis media, are a major reason for doctor visits among preschoolers in the U.S., accounting for more than 24 million trips a year to the family physician. The problem is a serious one with the treatment of children under two years of age for such infections having tripled between 1975 and 1990. Children who suffer from repeated ear infections before age six often experience temporary hearing loss, speech and language delays, coordination difficulties and, in some cases, permanent hearing loss. Likewise many infants, about 4 in 1000 births, have hearing impairment problems that cause delays in speech, language and cognitive development. In many instances, hearing loss is not detected until the child is two to three years old and not speaking properly. The present invention can also be adapted to screen for malfunctions in hearing among infants and children thereby providing early detection for both eye and ear problems.

A concern relating to testing or examinations using VEP is that the sampling rate of the VEP responses might not be synchronized with the periodic presentation of the visual stimulus. Failure to achieve such synchronization will make it difficult to read and interpret the resulting data and may lead to unreliable results as well as a possible wrong diagnosis. VEP responses that are not synchronized with the sampling rate require subjective, and therefore, unreliable analysis. Methods heretofore used to achieve such synchronization have employed external triggering signals to initiate data sampling, and therefore have lacked the capability of flexibility in the sampling rate and have resulted in large systems that were not compact and appealing for use by technicians and other medical personnel.

OBJECTS OF THE INVENTION

It is accordingly an object of the present invention to provide a system and method of synchronizing the VEP sampling rate with the presentation of the visual stimulus that overcomes the disadvantages of the prior techniques.

A more specific object of the present invention is to provide a system and method of synchronizing the VEP sampling rate with the presentation of visual stimulus by determining if a particular line of a line by line display of the stimulus pattern has been displayed and by generating interrupt request signals to the CPU of the computer that controls both the display of the stimuli and the sampling of VEP data in order to initiate and conduct sampling of-VEP data and to reflash the contents of a video RAM for the next frame of image displays.

Yet a further object of the present invention is to provide a system and method of synchronizing the VEP sampling rate with the presentation of the visual stimulus which utilizes commercially available components for generating interrupt signals and line counting.

Other objects, features and advantages of the invention will be apparent to those skilled in the art after appreciating the invention from the description hereinbelow.

SUMMARY OF THE INVENTION

The present invention is therefore directed to a system and method for performing vision examinations which includes displaying a series of visual stimuli in a line by line pattern display for observation by a patient and detecting the patient's visual evoked potentials in response to the visual stimuli. Electrical signals representative of the visual evoked potentials for each stimulus of each series of visual stimuli displayed is converted to digitized data, recorded and measured. The presentation of the visual stimulus is synchronized with the rate of sampling the responsive visual evoked potential signals by determining if a particular line of the line by line display has been displayed and by generating interrupt request signals on a computer in order to initiate and conduct the sampling of the visual evoked potential signals and to reflash the contents of a video RAM for the next frame of image displays.

The foregoing and other features, objects and advantages of the present invention are more fully described with reference to the following drawings annexed hereto.

DESCRIPTION OF THE PREFERRED EMBODIMENTS

Figure 1:
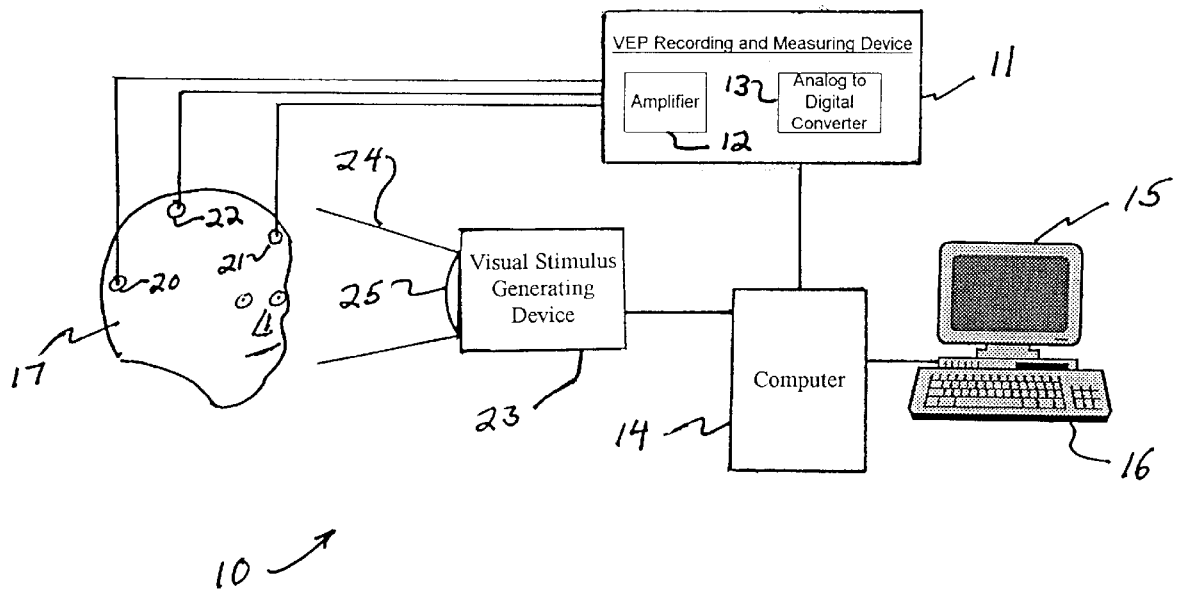
FIG. 1 is a block diagram illustrating the overall architecture of the present invention.

Generally, the system of the present invention incorporates a visual stimulator, data acquisition means with amplifiers to enhance VEP signals and a monitor to view results. Specifically, the system 10 of the present invention, as depicted in FIG. 1, includes a visual evoked potential recording and measuring device (or data acquisition component) 11 coupled to a central processing unit of a computer 14 for controlling the operations and functions of the VEP recording and measuring device 11. VEP recording and measuring device 11 includes an amplifier 12 for enhancing the VEP signals being acquired and an analog to digital converter 13 for converting the signals into a form for digital use. The amplifier is optically isolated for patient safety, has a high common mode rejection ratio, low noise and stability for low signal and frequency application. Computer 14 is coupled to a monitor 15 for displaying the data captured by the VEP recording and measuring device 11 and for providing a means to convey information concerning the operation of a test being conducted on a patient 17 to an operator. Keyboard 16, also connected to computer 14, provides a means to input information to the computer relating to a subject being tested. The responses in the brain to the stimuli are picked up by sensors attached non-invasively to the patient's scalp and are amplified, digitized, recorded and analyzed by the data acquisition component. Disposable electrodes 20, 21 and 22 are positioned on the scalp of the patient 17 over the visual cortex, the frontal cortex, and the parietal cortex, respectively. Electrodes 20, 21 and 22 are connected via hard wire to the VEP recording and measuring device 11. A visual stimulus generating device 23 is also connected to and controlled by computer 14 for generating visual stimuli to be perceived by the patient. A hood 24 may also be used and positioned between the stimulus generating device 23 and the patient 17 in order to enhance attention by the patient to the visual stimulus being displayed. The stimuli are highly variable arrays of one or two-dimensional light patterns. These stimuli can be rapidly modified or varied (i.e. at ~60 Hz or higher frame rate) and luminance contrast and main luminance can be altered through a full range of the gray scales from white to black. By permitting different regions of a pattern to be varied independently or contrasted with a static area, the system can make specific and detailed measurements of visual evoked potentials and perform all of the conventional visual evoked potential tests.

Figure 2:
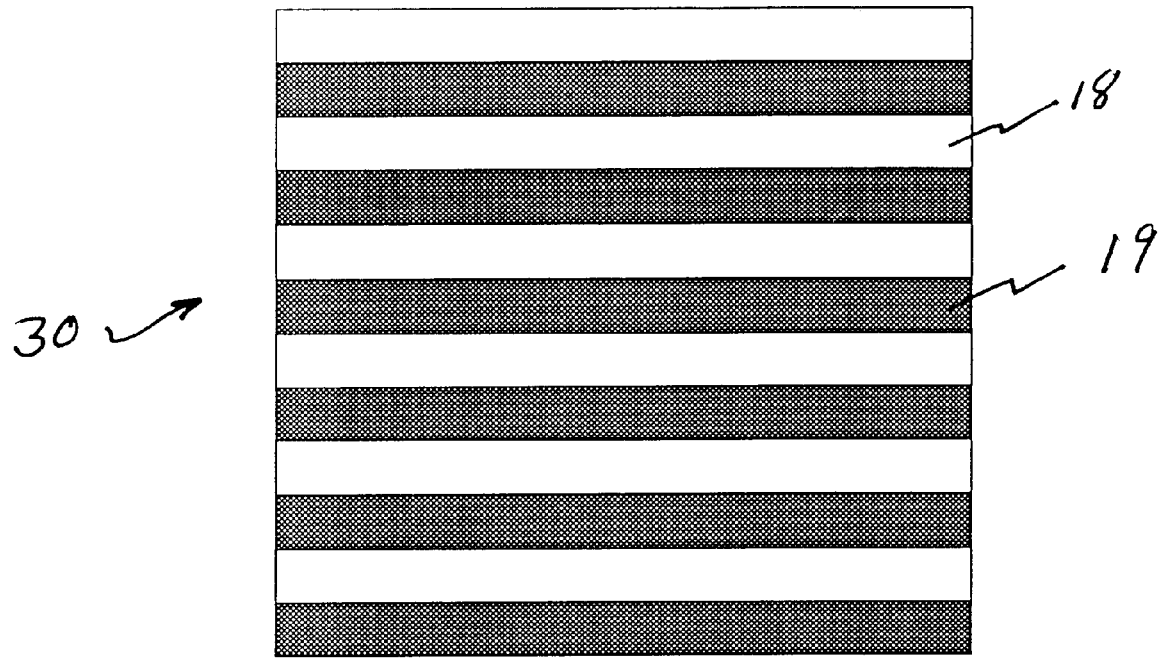
FIG. 2 is an illustration of one type of visual stimulus used in the present invention.

The present invention incorporates software carried by computer 14 for displaying a graphical user interface (GUI) on the monitor 15 upon initiation of the examination procedures. The GUI allows an operator to enter patient data such as name, date of birth, identification number, etc. After the patient data is entered into the system, the vision examination will begin with the presentation of visual stimuli on the stimulus display screen 25 of the stimulus device 23 for observation by the patient. The generation of the visual stimuli by device 23 is initiated and controlled by computer 14. The stimuli consists of sweeps of variable spatial patterns in the form of horizontal gratings that vary from thick to thin with the presentation of each such pattern lasting approximately one second. FIG. 2 illustrates an example of the type of stimulus display presented to the patient. The display consists of a pattern 30 of alternating and contrasting horizontally oriented light bands 18 and dark bands 19. The system of the invention causes the stimulus generating device 23 to present a series of patterns on the visual display screen 25. A series typically consists of six different patterns to be displayed. The display of each pattern lasts approximately one second. Each pattern differs from other patterns by the thickness of each band. In presenting the series, the first displayed pattern will have the thickest bands and each successive pattern displayed will have narrower bands. A number of sets of displays (each set consisting of five sweeps of a series) will be presented to the patient for observation by each eye of the patient. A set consists of five sweeps of a series, where a sweep is the continuous consecutive display of the six patterns of a series. By entering commands on an input device, such as keyboard 16 connected to computer 14, an operator may vary the series and sets of displays and after each series or set is complete, the operator can initiate presentation of a next series or set of displays. A set of displays will be presented to each of the eyes of the patient. Tracking information about each visual stimulus display will be presented on monitor screen 15 so that the operator will be able to track display activity. Upon completion of presentation of the sets of visual stimuli, the system of the invention will present the results of the tests on monitor screen 15.

A feature of the invention is the synchronization of the periodic visual stimulus and the sampling rate for recording the VEP signal responses using computerized technology. This method of synchronization includes use of interrupt request signals (IRQ) that are generated from a computer graphics card and an interrupt handling routine to sample the VEP responses and display the stimulus frame by frame at the same time. The IRQ signals generated from the graphics card are horizontal or vertical synch related signals. Thus, the IRQ signals are synchronized with the monitor frame rate. Using the IRQ signal as a timing control, the synchronization between the period of the stimulus and the VEP sampling rate is achieved.

Visual evoked potential signals, generated in response to visual stimulus, are digitized by the analog to digital converter 13 for computer processing. In order to analyze the VEP steady state response in a frequency domain and minimize the calculation error in the VEP Fourier components, the analog to digital conversion VEP sampling rate must be synchronized with the stimulus display. Once a periodic stimulus is presented to a subject, the VEP produced has a transient procedure at a certain starting period, for example 100 ms. After this period the VEP response reaches its steady state, that is, the response statistically becomes a repeatable periodic signal. A periodic signal can be expressed as a sum of sinusoids with various amplitudes, phases and multiple frequencies. These frequency components are referred to as Fourier components.

Figure 3:
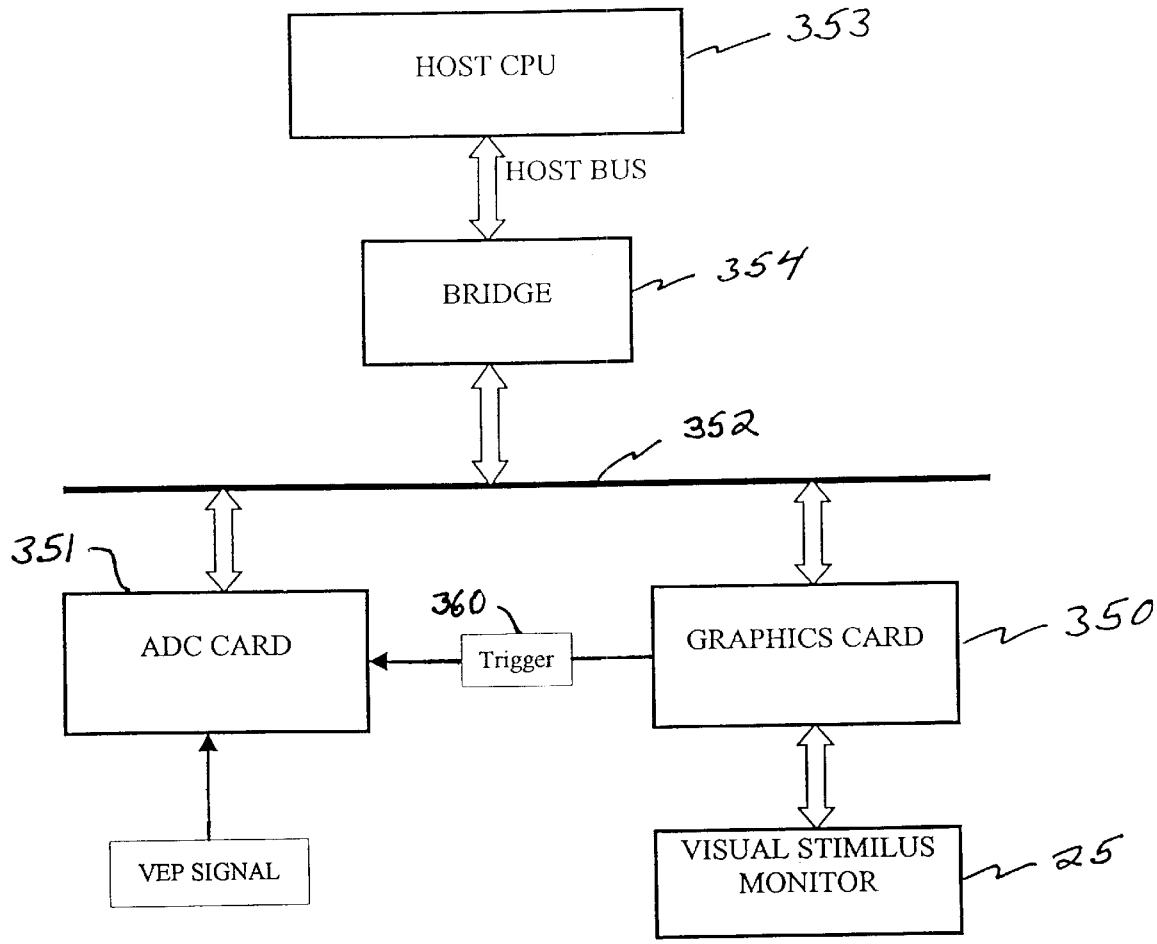
FIG. 3 is a block diagram illustrating a prior art architecture of a synchronization technique.

A conventional way to implement synchronization involves the use of triggering signals generated from a proprietary computer graphics card to activate analog to digital conversion of the VEP sampling. Such conventional technique is illustrated in FIG. 3. In this technique, a proprietary computer graphics card 350 interfaces with an analog to digital (also referred to as "ADC") conversion card 351. ADC card 351 and graphics card 350 interface with the computer via a computer bus 352 (such as an industry standard architecture (ISA) or a peripheral component interconnect (PCI) bus). When displaying the visual stimulus on the display screen 25, the graphics card 350 sends frame rate synchronized triggering signals to the ADC card 351. ADC card 351 records a sample of the VEP in response to the stimuli immediately when it receives each trigger. The frequency ratio of triggering signal and visual stimulus screen frame rate is preset by the computer on the graphics card 350 by means of which the synchronized sampling rate can be adjusted by the user. For example, the software on the computer can preset the trigger rate to be twice in one frame. So, if the frame rate is 75 Hz, then the sampling rate activated by the trigger is 150 Hz. The host CPU 353 of the computer is connected to the bus via a bridge 354. The graphics card 350 generates regular video signals to the visual stimulus display screen 25 for stimulus display. During the VEP sampling, graphics card 350 also generates frame rate synchronized triggers 360 which are transmitted to the ADC card 351 to trigger each data sampling.

Figure 4:
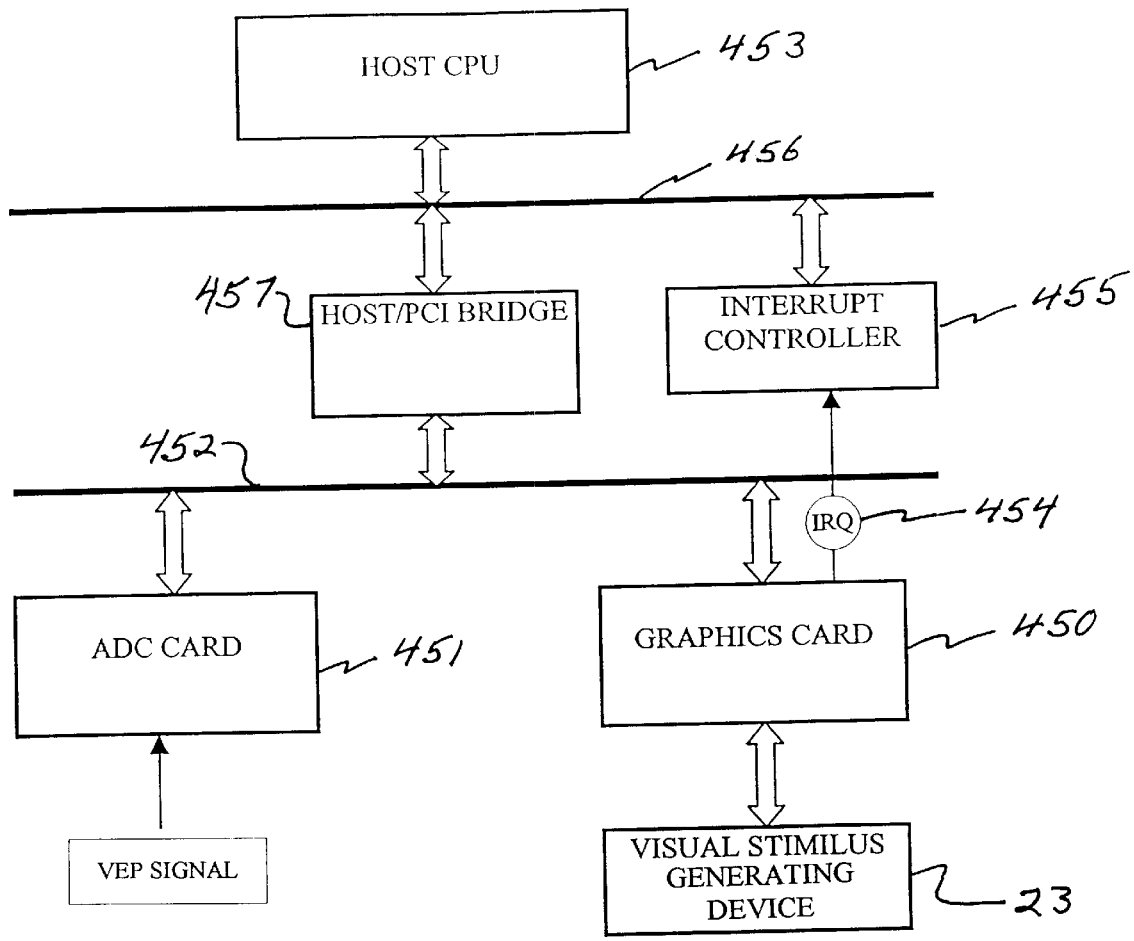
FIG. 4 is a block diagram illustrating the architecture of the synchronization system of the present invention.

FIG. 4 illustrates the architecture for the system of the present invention for synchronizing the VEP sampling rate with the visual stimulus. In this embodiment, no external triggering is required. Both the graphics card 450 and the ADC card 451 are commercially available products that interface with the computer CPU 453 through a standard PCI bus 452 and bridge 457. Graphics card 450 generates regular video signals to the visual stimulus generating device 23 for stimulus display of the patterns. Card 450 incorporates a line count register used to count the horizontal lines displayed on the display screen 25. During the VEP examining process, graphics card 450 further generates interrupt signals 454 (IRQ) via a commercially available interrupt controller 455. Interrupt controller 455 communicates with the computer CPU 453 across a host bus 456. The timing of the interrupt signals are determined by the display line count which can be set by the computer 14 on the graphics card 450. When the CPU 453 receives each interrupt signal from the graphics card 450, it suspends its current program and establishes an interrupt service/handling routine. In this routine, the CPU 453 activates the ADC card 451 to sample the VEP and reflashes the video RAM, i.e., loads the pattern data into the video card for the next frame display.

Graphics card 450 also has a line comparator. When the line count reaches the value set in the line comparator, card 450 generates the interrupt signal 454. By setting a predetermined value in the line comparator, the timing of the interrupt can be controlled by the computer. It also sets up the line count in the line comparator for the next interrupt signal.

Figure 5:
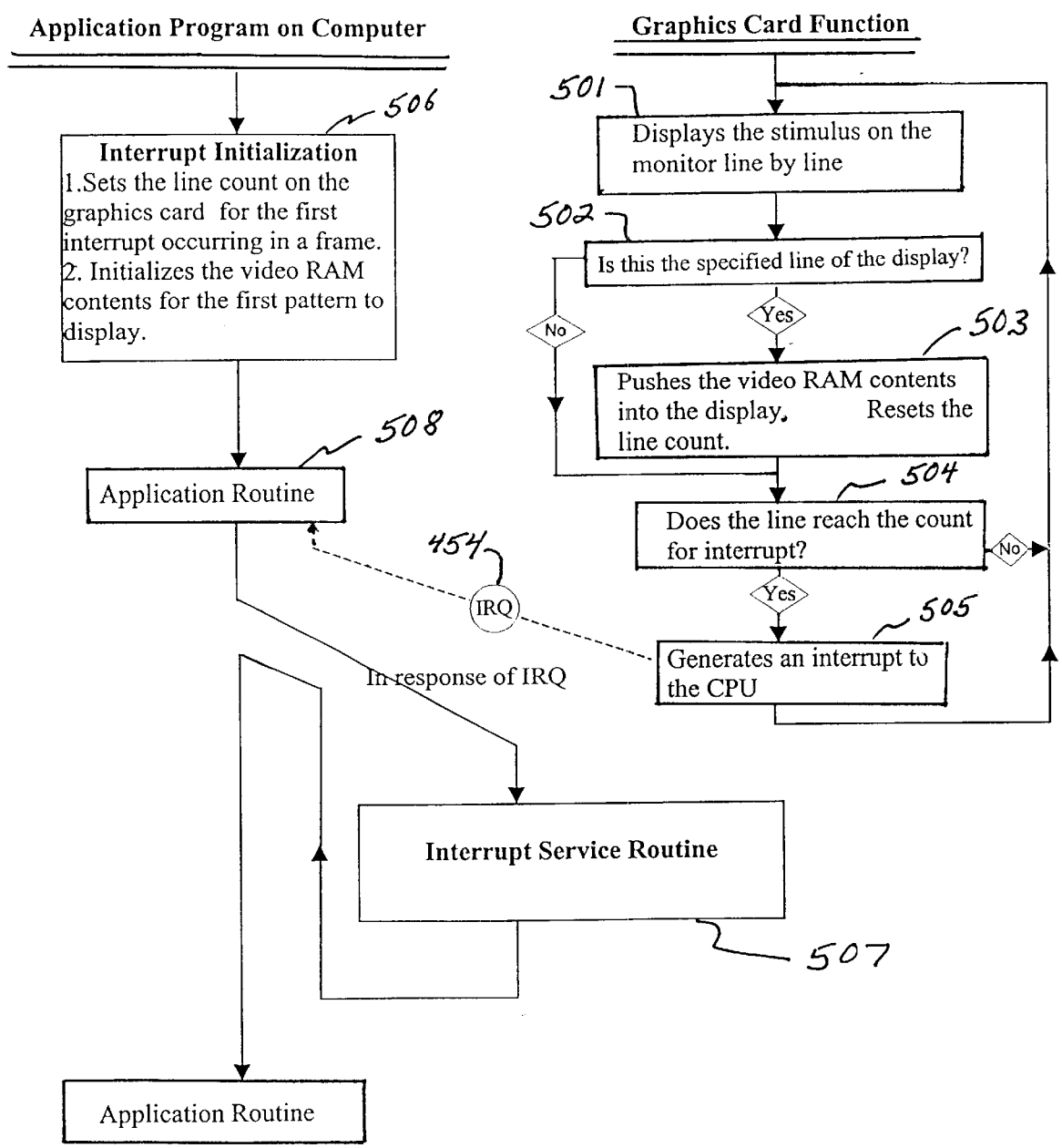
FIG. 5 is flow chart illustrating the process of synchronizing the visual evoked potential sampling rate with the visual stimulus.

Thus, the synchronization of presenting the stimulus with the data sampling is completely controlled by the system software without any hardware modifications. FIG. 5 illustrates the process of the interrupt technique for synchronizing the VEP sampling rate with the visual stimulus. At step 501, the graphics card initiates and conducts display of the stimulus on the visual stimulus monitor, line by line. Whether or not the specific or predetermined line of the visual image has been displayed is determined at step 502. If it has been, the video RAM contents are pushed into the display device 23/25 in order to display the pattern and the line count is reset to zero at step 503. If the predetermined specific line of the visual stimuli image has not been displayed, step 503 is skipped and step 504 determines whether or not the line of the visual image display has reached the preset count in the graphics card line comparator. If it has, then an interrupt request signal (IRQ) is generated to the computer CPU 453 (as indicated by dotted line 454). The application program 506 on the computer CPU 453 controls the interrupt initialization process. Program 506 sets the line count on the graphics card for the first interrupt occurring in a frame and initializes the video RAM content for the first pattern to display. Then the CPU generates the IRQ to the application routine 508 (for normal system operation and monitoring). When the CPU receives each interrupt signal generated from the graphics card, it suspends program 508 and goes to the interrupt service routine 507. In this routine, the computer activates the ADC card to sample the VEP and reflashes the contents of the video RAM for the next frame of pattern to be displayed.

Figure 6:
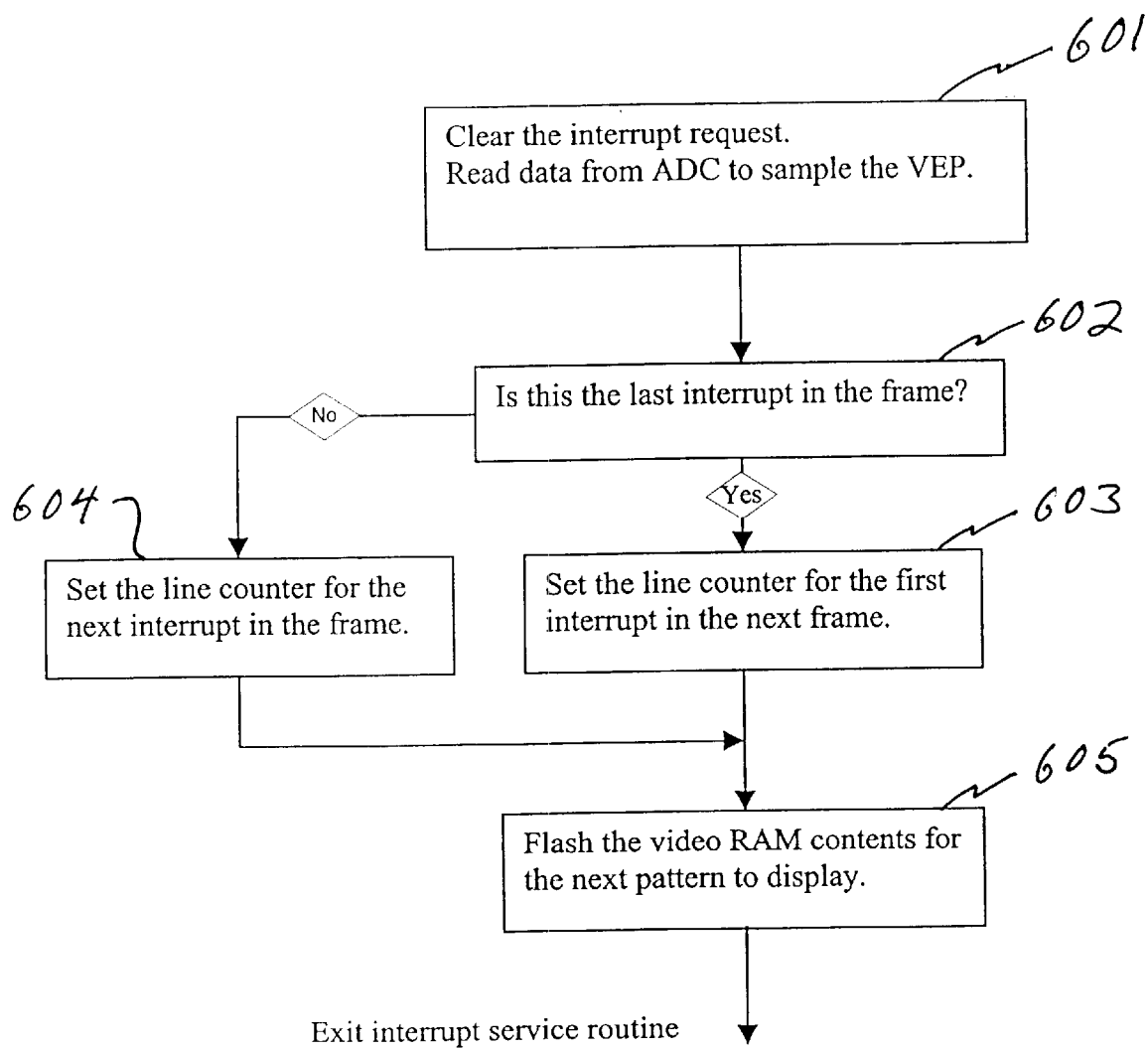
FIG. 6 is a flow chart illustrating the process of the interrupt service routine used in the present invention.

The interrupt service routine is described in connection with FIG. 6. The first step 601 clears the interrupt requests and reads data from the ADC card to sample the VEP. Whether this is the last interrupt in the frame is determined at step 602. If it is, the line counter is set for the first interrupt in the next frame at step 603 and if not, the line counter is set for the next interrupt in the same frame at step 604. In either event, the video RAM contents for the next visual image to be displayed is initiated at step 605 and the interrupt service routine is terminated and service returns to the application routine.

The invention has been described and illustrated in connection with certain preferred embodiments which illustrate the principals of the invention. However, it should be understood that various modifications and changes may readily occur to those skilled in the art, and it is not intended to limit the invention to the construction and operation of the embodiments shown and described herein. For example, the system and method of the invention are useful for a variety of medical examinations where sensory stimuli are used to produce evoked potentials from a patient in response to the stimuli. Such examinations might relate to auditory capability, ambulatory capability, neuro response and others, as well as vision capability. Accordingly, additional modifications and equivalents may be considered as falling within the scope of the invention as defined by the claims herein below.

What is claimed is:

1. A system for performing a medical examination comprising:
    means for presenting a series of sensory stimuli for perception by a patient;
    means for generating electrical signals representing said patient's evoked potentials in response to said sensory stimuli;
    means connected to said generating means for detecting said signals;
    means connected to said detecting means for amplifying said signals;
    means connected to said amplifying means for recording data representative of said signals;
    means connected to said recording means for measuring said data; and
    means connected to said measuring means for synchronizing the presentation of said series of sensory stimuli with the rate of sampling said evoked potential signals by generating interrupt request signals for initiating and conducting said sampling.

2. The system according to claim 1, wherein said medical examination is a vision examination and wherein said means for presenting said series of sensory stimuli comprises a computer operated visual stimulus generating device connected to a display screen for displaying a plurality of patterns for visual observation by a patient.

3. The system according to claim 2, wherein said plurality of patterns comprise contrasting horizontally oriented light and dark bands, each pattern of said plurality differing from the other patterns in a series by the thickness of each band.

4. The system according to claim 3, wherein said means for detecting said electrical signals comprises a plurality of electrodes connected to the scalp of a patient and coupled with a visual evoked potential recording and measuring device.

5. The system according to claim 4, wherein said means for amplifying said signals enhances said signals for data generation, and further comprising means for converting said signals to digitized data.

6. The system according to claim 5, wherein said means for synchronizing the presentation of said sensory stimuli with the rate of sampling said evoked potential signals comprises a computer graphics card for generating video signals to said visual stimulus generating device, said graphics card interfacing with the CPU of said computer and connected with said visual stimulus generating device, said graphics card including a line count register for counting horizontal lines displayed on said display screen, and an interrupt controller connected with said graphics card so that said graphics card generates interrupt request signals at predetermined time periods for initiating and conducting said data sampling.

7. The system according to claim 6, wherein said graphics card further includes a line comparator so that when said line count reaches a predetermined value in said line comparator, said graphics card generates said interrupt signal, the timing of said interrupt signal being controlled by said computer by predetermining said value in said line comparator.

8. A method for performing a vision examination comprising:
    displaying a series of visual stimuli for observation by a patient; said series comprising a plurality of a patterns presented line by line;
    detecting electrical signals representative of the patient's visual evoked-potentials in response to sensory perception of said visual stimuli;
    recording said electrical signals representative of said visual evoked potential for each stimulus of said series of visual stimuli displayed; and
    synchronizing said display of said series of visual stimuli with the rate of recording said electrical signals by generating interrupt request signals for initiating and conducting said recording.

9. The method according to claim 8, wherein said synchronizing comprises determining the display of a predetermined line of said line by line pattern display and generating said interrupt request signals to a computer for controlling said displaying in order to initiate recording of said visual evoked potential signals and to reflash the contents of a video RAM for the next frame of visual stimuli when said predetermined line has been detected.

10. The method according to claim 9, wherein said interrupt request signals are generated from a computer graphics card.

11. A method of synchronizing the presentation of a series of sensory stimuli with the rate of sampling visual evoked potential signals in response to visual perception of said sensory stimuli in a system for performing vision examinations having a visual stimuli generating device controlled by a computer graphics card with a line comparator in which said series of the sensory stimuli are a plurality of patterns, each pattern in said series comprising a line by line visual image and differing from the other pattern of said series, and in which said series is displayed to each eye of a patient for generating and detecting electrical signals representative of said patient's visual evoked potentials, said method of synchronizing comprising detecting the presentation of a particular line of said visual image, initiating display of a next pattern in said series upon detection of said predetermined line, resetting said line count to zero, detecting whether a preset count in said graphics card line comparator has been reached, and generating an interrupt request signal to the CPU of said computer.

* * * * *